(12) United States Patent
Cryder et al.

(10) Patent No.: US 9,848,863 B2
(45) Date of Patent: Dec. 26, 2017

(54) SURGICAL RETRACTOR SYSTEMS AND METHODS

(71) Applicant: GLOBUS MEDICAL, INC., Audubon, PA (US)

(72) Inventors: Joel Cryder, Chalfont, PA (US); Edward Karpowicz, Sewell, NJ (US); Matthew Kohler, East Greenville, PA (US)

(73) Assignee: Globus Medical, Inc, Audubon, PA (US)

( * ) Notice: Subject to any disclaimer, the term of this patent is extended or adjusted under 35 U.S.C. 154(b) by 485 days.

(21) Appl. No.: 14/630,684

(22) Filed: Feb. 25, 2015

(65) Prior Publication Data

US 2016/0242756 A1 Aug. 25, 2016

(51) Int. Cl.
| | |
|---|---|
| A61B 1/32 | (2006.01) |
| A61B 17/02 | (2006.01) |
| A61B 17/00 | (2006.01) |
| A61B 17/22 | (2006.01) |
| A61B 90/57 | (2016.01) |
| A61B 17/28 | (2006.01) |

(52) U.S. Cl.
CPC .......... *A61B 17/0206* (2013.01); *A61B 17/02* (2013.01); *A61B 90/57* (2016.02); *A61B 2017/0046* (2013.01); *A61B 2017/00477* (2013.01); *A61B 2017/00858* (2013.01); *A61B 2017/22074* (2013.01); *A61B 2017/2837* (2013.01)

(58) Field of Classification Search
None
See application file for complete search history.

(56) References Cited

U.S. PATENT DOCUMENTS

| | | |
|---|---|---|
| 1,437,995 A | 12/1922 | Richter |
| 1,612,446 A | 12/1926 | Larson |
| 2,012,597 A | 8/1935 | Cameron |
| 2,285,956 A | 6/1942 | Weber |
| 2,460,555 A | 2/1949 | Voigtlander |
| 4,896,661 A | 1/1990 | Bogert et al. |
| 5,529,571 A | 6/1996 | Daniel |
| 5,788,630 A | 8/1998 | Furnish |
| 5,846,193 A | 12/1998 | Wright |
| 5,893,831 A | 4/1999 | Koros et al. |
| 5,931,777 A | 8/1999 | Sava |
| 5,944,658 A | 8/1999 | Koros et al. |
| 5,984,865 A | 11/1999 | Farley et al. |
| 6,042,540 A | 3/2000 | Johnston et al. |
| 6,261,296 B1 | 7/2001 | Aebi et al. |
| 6,551,316 B1 | 4/2003 | Rinner et al. |
| 6,663,562 B2 | 12/2003 | Chang |
| 6,712,825 B2 | 3/2004 | Aebi et al. |
| 6,733,444 B2 | 5/2004 | Phillips |
| 6,736,775 B2 | 5/2004 | Phillips |
| 6,834,837 B2 | 12/2004 | Schilt et al. |
| 7,179,225 B2 | 2/2007 | Shluzas et al. |
| 7,371,955 B2 | 5/2008 | Takegawa |
| 7,455,639 B2 | 11/2008 | Ritland |
| 7,473,223 B2 | 1/2009 | Fetzer |

(Continued)

*Primary Examiner* — Sameh Boles

(57) ABSTRACT

Embodiments herein are generally directed to surgical retractor systems. In some embodiments, these retractor systems may be used in spinal fusion or other procedures that utilize a transforaminal approach.

20 Claims, 9 Drawing Sheets

(56) References Cited

U.S. PATENT DOCUMENTS

| | | |
|---|---|---|
| 7,494,463 B2 | 2/2009 | Nehls |
| 7,588,537 B2 | 9/2009 | Bass |
| 7,758,584 B2 | 7/2010 | Bankoski et al. |
| 8,226,554 B2 | 7/2012 | McBride et al. |
| 8,251,901 B2 | 8/2012 | White et al. |
| 8,257,255 B2 | 9/2012 | Farley et al. |
| 8,353,826 B2 | 1/2013 | Weiman |
| 8,360,971 B2 | 1/2013 | Farley et al. |
| 8,414,625 B2 | 4/2013 | Gorek |
| 8,535,320 B2 | 9/2013 | Woolley et al. |
| 8,597,180 B2 | 12/2013 | Copeland et al. |
| 8,636,656 B2 | 1/2014 | Nichter et al. |
| 8,876,709 B2 | 11/2014 | Vayser et al. |
| 8,974,381 B1 | 3/2015 | Lovell et al. |
| 2007/0213596 A1 | 9/2007 | Hamada |
| 2009/0018399 A1 | 1/2009 | Martinelli et al. |
| 2009/0105547 A1 | 4/2009 | Vayser et al. |
| 2009/0124861 A1 | 5/2009 | Fetzer |
| 2009/0221877 A1 | 9/2009 | Woods |
| 2009/0264710 A1 | 10/2009 | Chana et al. |
| 2010/0113885 A1 | 5/2010 | McBride et al. |
| 2011/0130634 A1 | 6/2011 | Solitario, Jr. et al. |
| 2012/0271118 A1 | 10/2012 | White |
| 2012/0296171 A1* | 11/2012 | Lovell ................ A61B 17/0206 600/213 |
| 2012/0296172 A1 | 11/2012 | Raven, III et al. |
| 2013/0095387 A1 | 4/2013 | Kawamura et al. |
| 2013/0123581 A1 | 5/2013 | Fritzinger et al. |
| 2014/0121704 A1 | 5/2014 | Solitario, Jr. |

* cited by examiner

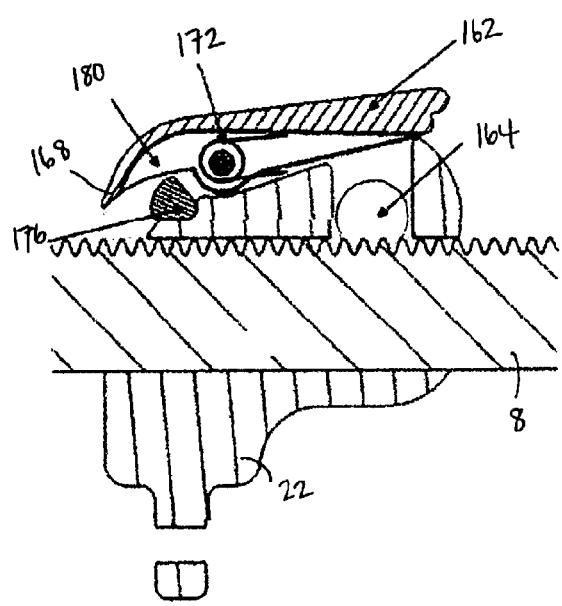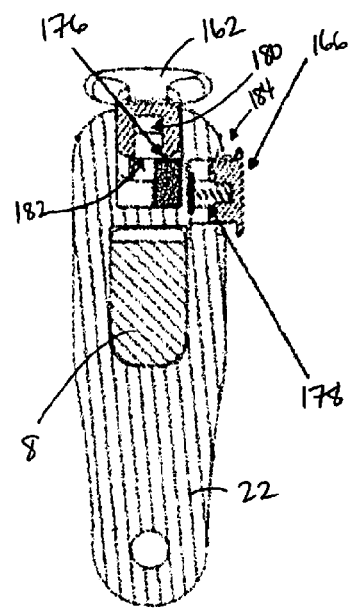
FIGURE 5D
FIGURE 5E
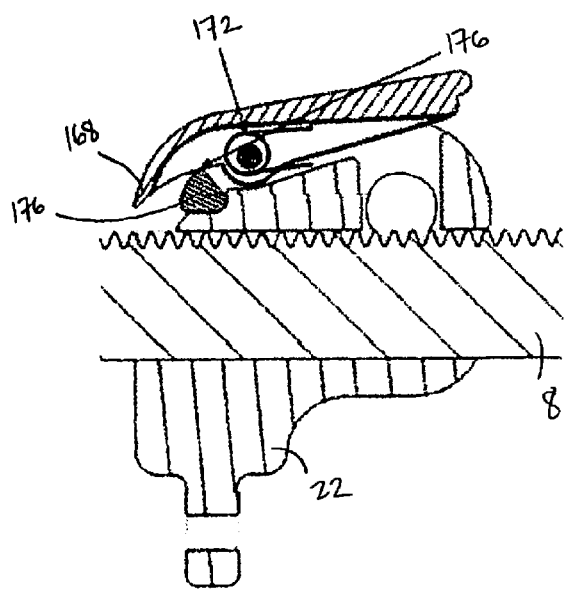
FIGURE 5F

SURGICAL RETRACTOR SYSTEMS AND METHODS

FIELD OF THE INVENTION

The present invention relates to systems for performing surgical retraction and methods of use thereof.

BACKGROUND OF THE INVENTION

Many types of spinal irregularities can cause pain, limit range of motion, or injure the nervous system within the spinal column. These irregularities can result from, without limitation, trauma, tumor, disc degeneration, and disease. Often, these irregularities are treated through a surgical procedure that may include, for example, immobilizing a portion of the spine. These treatments may involve replacing a damaged disc with an intervertebral implant and securing the adjacent vertebrae with a combination of screws and rods.

In order to perform these procedures, a surgical opening is created, and a device such as a retractor may be used to enlarge the opening and facilitate access to the surgical site. The retractor may typically include one or more blades that can be adjusted to establish, provide, and/or maintain an appropriate opening that minimizes trauma to surrounding tissue.

SUMMARY OF THE INVENTION

Some embodiments herein are directed to a retractor system that can include a first arm comprising a towing assembly, the towing assembly comprising an interface member coupled to a rotatable shaft, wherein the interface member comprises a distal surface having a plurality of protrusions and receptacles; and a first blade comprising a through-hole passing from a first side surface to a second side surface and configured to reversibly receive the rotatable shaft therein, wherein the first blade comprises a plurality of protrusions and receptacles configured to intermesh with the plurality of protrusions and receptacles of the distal surface of the first arm.

Other embodiments herein are directed to a retractor system that can include a first arm comprising a towing assembly, the towing assembly comprising a rotatable shaft coupled to both a worm drive and an interface member, the interface member comprising a star grind; a first blade comprising a through-hole passing from a first side surface to a second side surface and configured to reversibly receive the rotatable shaft therein, an interiorly-threaded passageway that intersects the through-hole, and a star grind on the first side surface configured to interdigitate with the star grind of the first arm; and a retaining member configured to reversibly engage the interiorly-threaded opening of the first blade and the rotatable shaft of the first arm.

Yet other embodiments herein are directed to a retractor system that can include a first arm comprising a towing assembly, the towing assembly comprising a rotatable shaft coupled to both a worm drive and an interface member, the interface member comprising a star grind; and a first blade comprising a through-hole configured to reversibly receive the rotatable shaft therein and a star grind configured to interdigitate with the star grind of the first arm; wherein the first blade is configured to be pivotable relative to the first arm by an angle of at least 180 degrees when the first blade is coupled to the first arm.

Some embodiments herein are directed to a method of operating a retractor system that can include providing a retractor system, comprising: a first arm comprising a towing assembly, the towing assembly comprising an interface member coupled to a rotatable shaft, wherein the interface member comprises a distal surface having a plurality of protrusions and receptacles; and a first blade comprising a through-hole configured to receive the rotatable shaft therein and a first side surface having a plurality of protrusions and receptacles, wherein the first side surface is configured to intermesh with the distal surface of the first arm; reversibly coupling a first handle to the first blade; reversibly coupling the first blade to the first arm, comprising: inserting the rotatable shaft of the first arm into the through-hole of the first blade; and threading a set screw through a passageway on the first blade; and actuating the towing assembly to tow the first blade relative to the first arm.

Other embodiments herein are directed to a method of operating a retractor system that can include providing a retractor system, comprising: a first arm comprising a towing assembly, the towing assembly comprising a rotatable shaft coupled to both a worm drive and an interface member having a star grind thereon; a first blade comprising a through-hole configured to reversibly receive the rotatable shaft therein, an interiorly-threaded opening that intersects the through-hole, and a first side surface having a star grind configured to interdigitate with the star grind of the first arm; and a retaining member configured to reversibly engage the interiorly-threaded opening of the first blade and the rotatable shaft of the first arm; reversibly coupling a first handle to the first blade; reversibly coupling the first blade to the first arm, comprising: inserting the rotatable shaft of the first arm into the through-hole of the first blade; threading the retaining member in the interiorly-threaded passageway and into engagement with the rotatable shaft of the first arm; and interdigitating the star grind of the first arm with the star grind of the first blade; and actuating the worm drive to tow the first blade relative to the first arm.

Yet other embodiments herein are directed to a method of operating a retractor system that can include providing a retractor system, comprising: a first arm comprising a towing assembly, the towing assembly comprising a rotatable shaft coupled to both a worm drive and an interface member, the interface member comprising a star grind; and a first blade comprising a through-hole configured to reversibly receive the rotatable shaft therein and a first side surface having a star grind thereon, the star grind of the first surface configured to interdigitate with the star grind of the first arm; reversibly coupling the first blade to the first arm, comprising inserting the rotatable shaft of the first arm into the through-hole of the first blade and interdigitating the star grind of the first arm with the star grind of the first blade; and actuating the worm drive to pivot the first blade relative to the first arm by an angle in the range of from 1 degree to 360 degrees.

Further areas of applicability of the present invention will become apparent from the detailed description provided hereinafter. It should be understood that the detailed description and specific examples, while indicating certain embodiments of the invention, are intended for purposes of illustration only and are not intended to limit the scope of the invention.

BRIEF DESCRIPTION OF THE DRAWINGS

The present embodiments will become more fully understood from the detailed description and the accompanying drawings, wherein:

FIGS. 5B-F illustrates cross-sectional views of a ratcheting assembly as described herein.

DETAILED DESCRIPTION

Figure 1A:
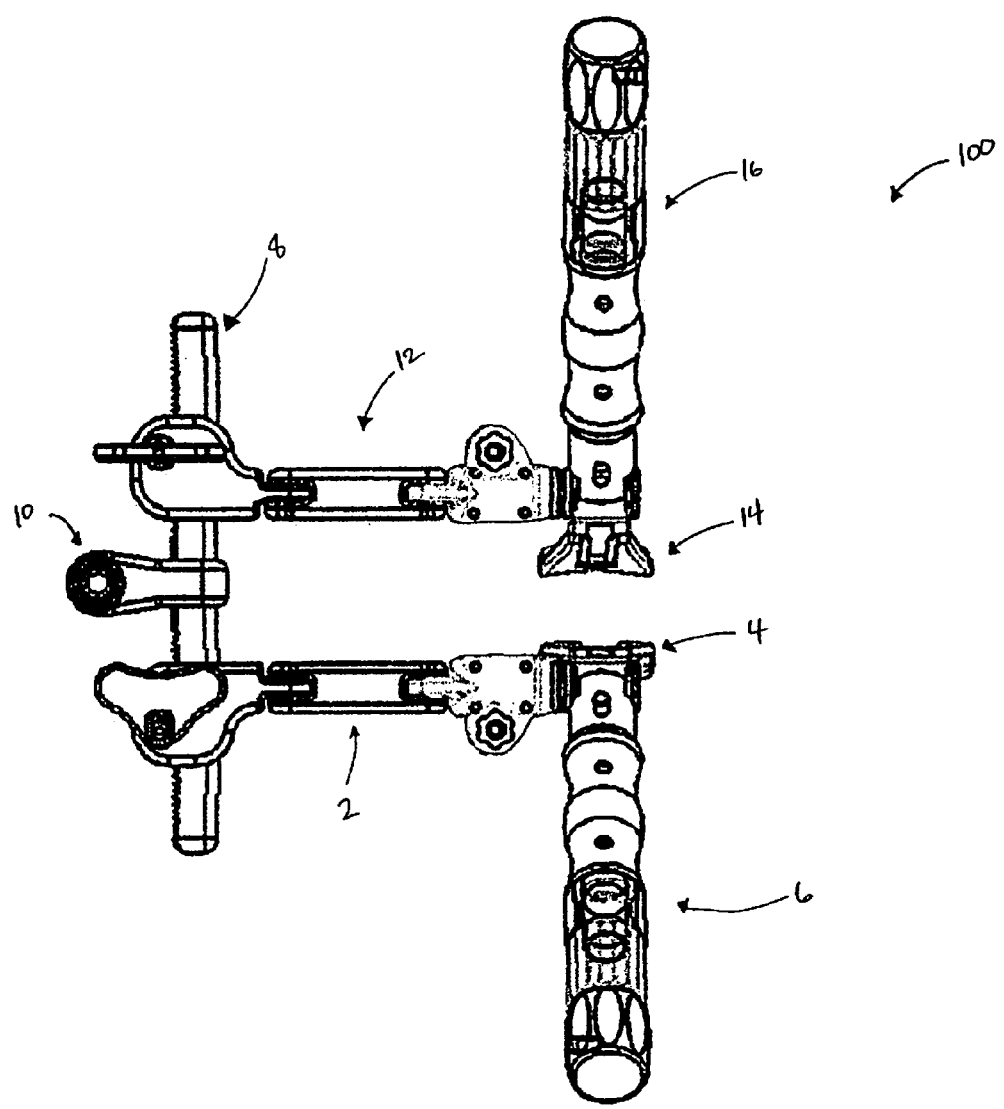
FIGS. 1A-B illustrate perspective views of a retractor assembly as described herein.

In a spinal fusion procedure, a damaged spinal disc may be removed and replaced with an intervertebral implant (e.g., a cage, spacer, vertebral body replacement, or other prosthetic). The adjacent vertebrae may be stabilized with a combination of screws and rods. As part of the procedure, a retractor may be used to establish, enlarge, manipulate, and/or maintain a surgical opening, thereby facilitating the passage of the various implant devices and related tools. In some instances, different retractors may be used for different surgical approaches (e.g., anterior, posterior, transforaminal, lateral), due to the varying anatomical features unique to each approach. For example, in a midline incision transforaminal (e.g., TLIF) approach, the multifidis muscle may need to be separated from the spinous process and retracted out laterally on both sides to the lamina. The retractor blades may thus be used to hold back soft tissue and muscle, and precise angling of the retractor's blades may depend at least in part on various factors, including the particular patient's anatomy and surgeon's preference. Accordingly, described herein are new and improved retractor systems that can enable retraction in a manual, handheld configuration as well as in a mounted, linear configuration. Further described herein are new and improved retractor systems that include a blade that can be towed or pivoted by up to 360 degrees or more relative to an arm of the system. Overall, retractor systems disclosed herein may advantageously provide improved blade manipulation, resulting in more precise tissue retraction. Although described herein with regards to midline TLIF procedures, those skilled in the art may appreciate that the retractor systems described herein may also be used in other surgical procedures.

Components of all of the devices disclosed herein can be made of materials known to those skilled in the art, including metals (e.g., titanium), metal alloys (e.g., stainless steel and cobalt-chromium), ceramics, polymers (e.g., poly ether ether ketone (PEEK), polyphenylene sulfone (PPSU), polysulfone (PSU), polycarbonate (PC), polyetherimide (PEI), polypropylene (PP), polyacetals, or mixtures or co-polymers thereof), allograft, and/or combinations thereof. In some embodiments, the devices may include radiolucent and/or radiopaque materials. The components can also be machined and/or manufactured using techniques known to those skilled in the art. For example, polymeric components may be injection-molded or blow-molded.

As used herein the terms "proximal" and "distal" are utilized generally with reference to a user (e.g., a surgeon) of the retractor assemblies described herein. When used with reference to a rack, described further herein, the terms "lateral" and "medial" refer generally to the ends and the middle of the rack, respectively. For example, a retractor arm traveling in a lateral direction may be traveling from a middle portion of the rack to an end portion of the rack, and a retractor arm traveling in a medial direction may be traveling from an end portion of the rack to a middle portion of the rack. These and other directional terms such as "superior," "inferior," "top," and "bottom," and the like may be used herein for descriptive purposes and do not limit the orientation(s) in which the devices may be used.

Turning now to FIGS. 1A-5F, a retractor system 100 is illustrated in accordance with embodiments described herein. As illustrated in FIGS. 1A-B, the retractor system 100 can include a first arm 2 and a first blade 4. In some embodiments, the retractor system 100 may also include a second arm 12 and a second blade 14. The retractor system 100 may optionally include one or more additional components, such as a first handle 6, a rack 8, and/or a second handle 16, as described herein. The retractor system 100 may also include a table mount 10. In use, the first and second arms 2, 12 may be configured to translate at least laterally along the rack 8, and may thereby be configured to linearly retract tissue and/or maintain or enlarge a surgical window. Those skilled in the art may appreciate that the second arm 12 and second blade 14 may include some or all of the same features as the first arm 2 and first blade 4, respectively. Thus, those skilled in the art may appreciate that any description of the first arm 2 and first blade 4 herein may also apply to the second arm 12 and second blade 14.

Figure 2A:
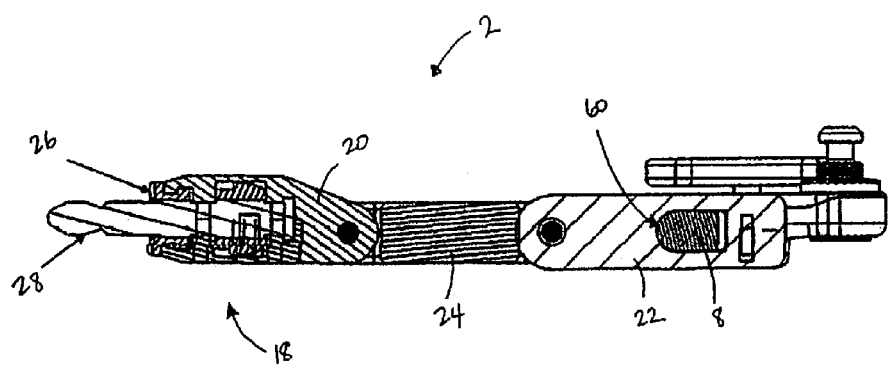
FIG. 2A illustrates a cross-sectional view of a first arm as described herein.

As illustrated in FIG. 2A, the first arm 2 can include a towing assembly 18. In some embodiments, the first arm 2 may be jointed. In these embodiments, the first arm 2 can also include a body 20, a base 22, and a connector 24 pivotably coupled therebetween. In some embodiments, the towing assembly 18 can be at least partially located or housed within the body 20. In other embodiments, the towing assembly 18 may be at least partially located or housed within another part of the first arm 2 (e.g., the base 22 and/or the connector 24).

Figure 2B:
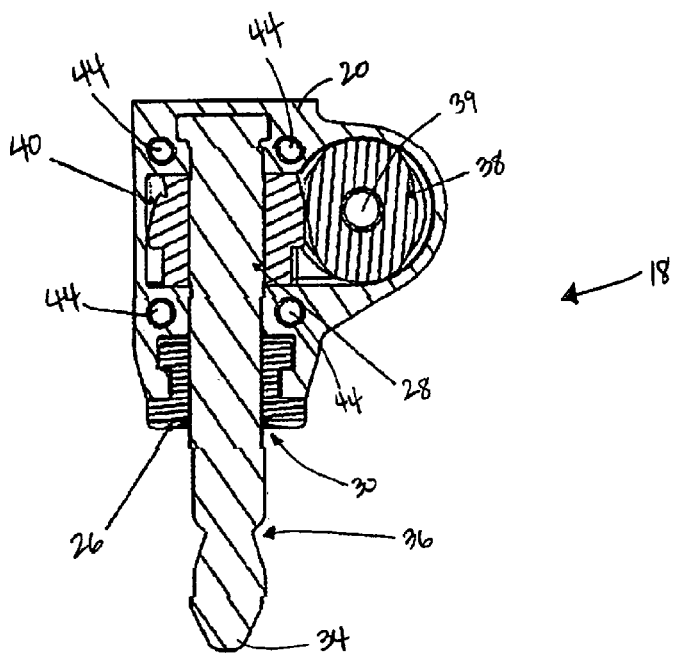
FIG. 2B illustrates a cross-sectional view of a towing assembly as described herein.

As illustrated in FIGS. 2A-B, the towing assembly 18 can include an interface member 26 and a rotatable shaft 28. The rotatable shaft 28 can be generally elongate and/or cylindrical, and can include a tapered distal tip 34, as illustrated in FIG. 2B. The rotatable shaft 28 can be configured to rotate about a longitudinal axis. The rotatable shaft 28 can also include a reduced-diameter section. For example, the rotatable shaft 28 can also include a circumferential channel or groove 36 on an exterior surface thereof. The groove 36 may extend partially or entirely around the circumference of the rotatable shaft 28.

The rotatable shaft 28 may be coupled to the interface member 26, for example, by passing through an axial hole 30 of the interface member 26. The axial hole 30 may extend longitudinally along an entire length of the interface member 26. In some embodiments, the interface member 26 may be configured to rotate with the rotatable shaft 28, but not relative to (e.g., separately from) the rotatable shaft 28.

Figure 2C:
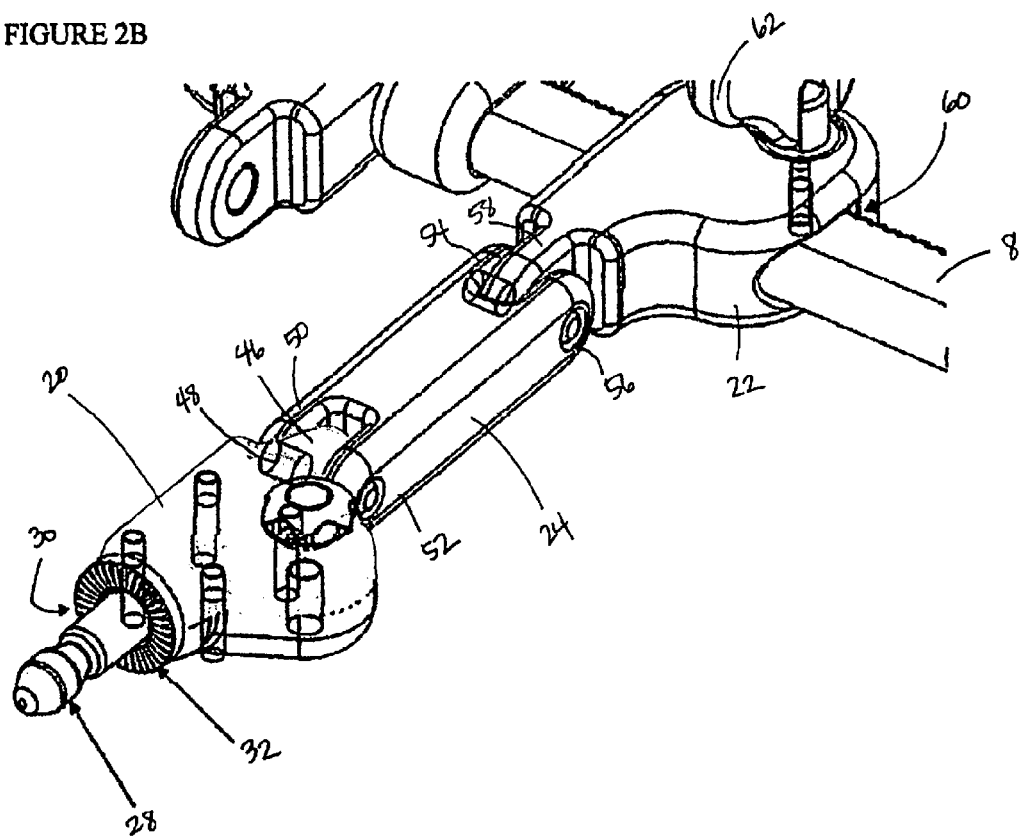
FIG. 2C illustrates a perspective view of a first arm coupled to a rack as described herein.

The interface member 26 can include an outer (e.g., distal and/or planar) surface 32 that includes a plurality of protrusions (e.g., bumps, peaks, teeth, and/or ridges) and/or receptacles (e.g., valleys, channels, depressions, and/or grooves)

which may be interspersed therebetween, as illustrated in FIG. 2C. In some embodiments, the protrusions and receptacles may extend radially outward from the axial hole 30. As illustrated in FIG. 2C, the distal surface 32 can include a plurality of ridges and grooves extending radially around an opening of the axial hole 30. As described herein, the plurality of protrusions and receptacles may be referred to as a star grind.

In alternative embodiments, an outer surface of the rotatable shaft 28, rather than the outer surface 32 of the interface member 26, may include a plurality of protrusions and/or receptacles. In these embodiments, the rotatable shaft 28 may include an external spline (e.g., a plurality of protrusions and/or receptacles) extending longitudinally along an external surface thereof.

Figure 2D:
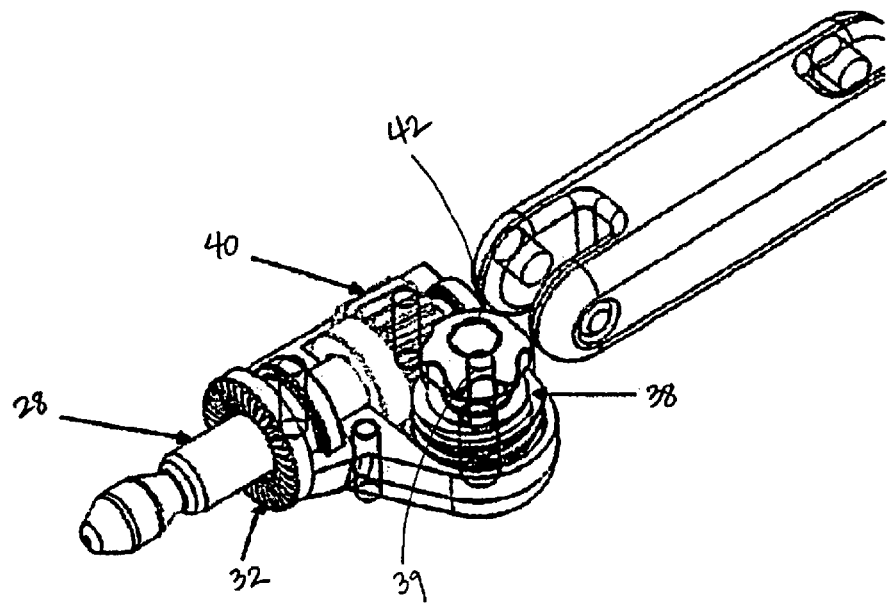
FIG. 2D illustrates a perspective view of a first arm as described herein.

The towing assembly 18 can further include a gear assembly that includes two or more gear members. The gear assembly can be configured to apply torque or a rotational force to the rotatable shaft 28. In some embodiments, the gear members may include parallel axes of rotation, and in other embodiments, the gear members may include perpendicular or orthogonal axes of rotation. As illustrated in FIG. 2B, the towing assembly 18 can include a worm drive, wherein the worm drive can include a worm 38 and a worm gear 40. As illustrated in FIG. 2D, the worm 38 may include a plurality of threads configured to mesh with teeth of the worm gear 40. The worm gear 40 may be, for example, a spur gear or a helical gear. In some embodiments, other types of gears and/or other gear arrangements may be used.

The worm gear 40 may be coupled to the rotatable shaft 28. As illustrated in FIGS. 2B and 2D, for example, the rotatable shaft 28 may be configured to pass through an axial hole in the worm gear 40. In some embodiments, the worm gear 40 may be configured to rotate with the rotatable shaft 28, but not relative to (e.g., separately from) the rotatable shaft 28. As illustrated in FIG. 2D, the worm 38 may be configured to couple with or engage an actuator, such as a bolt, screw, pin, or hex head 42. In some embodiments, both the worm 38 and the actuator 42 may be coupled to a post 39, illustrated in FIGS. 2B and 2D. The hex head 42 may be configured to engage a driver such as a screwdriver, wrench, Allen wrench, or hex driver. The actuator may include a socket configured to receive a portion of the driver therein. For example, hex head 42 may include a hexagonal recess; however, those skilled in the art may appreciate that other actuators having alternatively-shaped engagement recesses (e.g., square, triangular, pentagonal, heptagonal, and/or octagonal) may be used. In some embodiments, the socket may have a width in the range of from about 5 mm to about 10 mm. Those skilled in the art may appreciate that, in use, a surgeon or other practitioner may use a driver to apply a rotational force in a first direction to the worm 38, which may then cause the worm gear 40 and the rotatable shaft 28 to rotate in a first direction. Application of rotational force in a second, opposite direction may also cause the rotatable shaft 28 to rotate in a second direction opposite the first.

In use, the worm gear 40 and the interface member 26 may be coupled to the rotatable shaft 28 and subsequently placed into the body 20. In some embodiments, the body 20 may include a two-piece construction with top and bottom members secured by a plurality of set screws or pins 44, as illustrated in FIG. 2B. In other embodiments, the body 20 may include a one-piece construction (e.g., a unitary body). The body 20 may also include a cavity configured to receive at least a portion of the towing assembly 18 therein. The body 20 may be pivotably connected to the connector 24. As illustrated in FIG. 2C, the body 20 can include a proximal projection 46. The proximal projection 46 can include a hole passing transversely therethrough. The transverse hole can be configured to receive an elongate fastener such as pin 48 therein.

As illustrated in FIG. 2C, the connector 24 can include first and second distal prongs 50, 52 that are separated by a distal recess. Each of the prongs 50, 52 can include a hole passing transversely therethrough. The holes may be coaxial. As illustrated in FIG. 2C, the holes may be configured to receive pin 48 or other fastener therein. In use, those skilled in the art may appreciate that the body 20 may be pivotably coupled to the connector 24 by inserting the proximal projection 46 into the distal recess between distal prongs 50, 52, and inserting pin 48 into the resulting transverse passageway.

The connector 24 can also include first and second proximal prongs 54, 56 that are separated by a proximal recess. Each of the prongs 54, 56 can include a hole passing transversely therethrough. The holes may be coaxial and may be configured to receive a pin or other fastener therein. The connector 24 may be pivotably coupled to the base 22 in a manner similar to that described with respect to the body 20. For example, the base 22 can include a distal projection 58. The distal projection 58 can include a hole passing transversely therethrough and that can be configured to receive a pin or other elongate fastener therethrough. In use, the distal projection 58 of the base 22 can be inserted into the proximal recess of the connector 24, between proximal prongs 54, 56. A pin or other elongate fastener may then be inserted into the resulting transverse passageway.

Figure 1B:
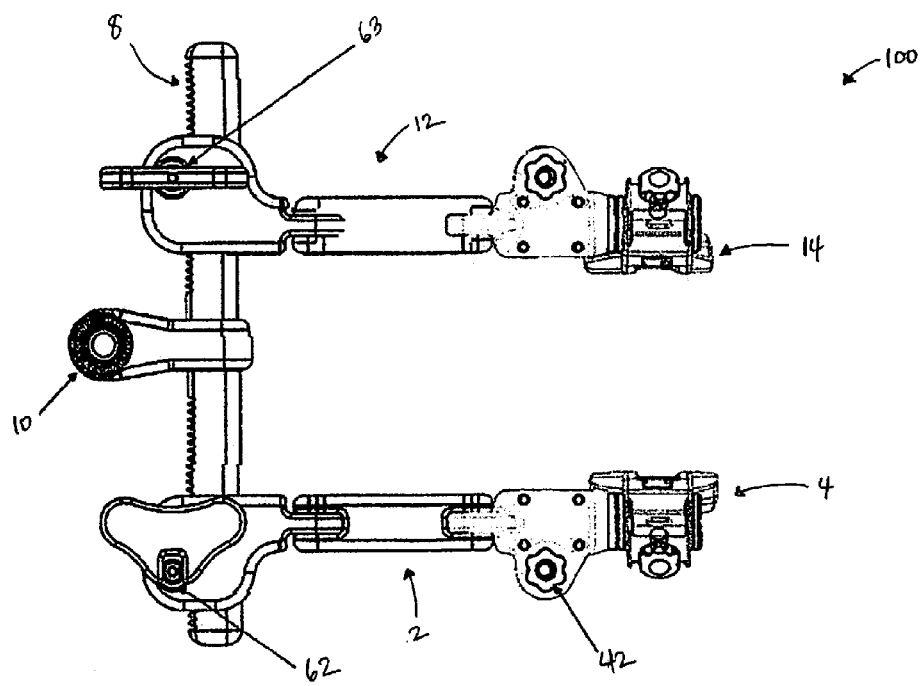

The arm 2 may be coupled to and/or may be configured to translate linearly along a guide member, such as a rail, track, and/or rack 8, as illustrated in FIG. 2C. The arm 2 may be configured to translate in two directions (e.g., medial and lateral) along the rack 8. The rack 8 may be an elongate bar extending along a linear axis, and may include a plurality of teeth extending longitudinally thereon. The teeth may be symmetrical or asymmetrical (e.g., slanted). In some embodiments, the base 22 may be configured to couple the first arm 2 to the rack 8. For example, the base 22 may include a channel or passageway 60 configured to receive the rack 8 therein, as illustrated in FIGS. 2A and 2C. The base 22 can also include a translation member that can be configured to translate the arm 2 along the rack 8. In some embodiments, the translation member can include a gear member, such as a pinion or other circular gear, described further herein. The gear member can include gear teeth that mesh with the gear teeth on the rack 8. The gear teeth may be symmetrical or asymmetrical (e.g., slanted). The base 22 may also include an actuator 62, which may include a grip, handle, butterfly screw, or knob, as illustrated in FIGS. 1B and 2C. The actuator 62 may be configured to be coupled to the translation member. In use, rotation of the actuator 62 may cause the translation member to rotate. The rotational motion may be converted to linear motion as the translation member translates along the rack 8. In some embodiments, the actuator 62 may be tiltable or pivotable. This may reduce the profile of the actuator 62, which can be advantageous in environments where space may be limited.

The base 22 can also include a locking member, such as a clamp. In some embodiments, the actuator 62 may be coupled to the locking member. In some embodiments, the locking member may be configured to lock and/or secure the first arm 2 at a particular lateral position along the rack 8 and may prevent and/or inhibit further motion or translation relative to the rack 8. In other embodiments, the locking member may prevent and/or inhibit motion or translation in a single direction along the rack 8 (e.g., medially relative to the rack).

In some embodiments, the base 22 may include a lever, such as a pawl, that is configured to engage the teeth on the rack 8. The pawl may be spring-loaded and may allow motion of the arm 2 in a first direction along the rack 8 while also preventing and/or inhibiting motion of the arm 2 in a second direction along the rack 8 (e.g., medially relative to the rack 8). In these embodiments, the arm 2 may translate laterally to retract tissue, but may be prevented from returning towards its original position on the rack 8. In some embodiments, the pawl may be configured to be disengageable so that the arm 2 may be allowed to translate in a second direction. For example, the pawl may be disengaged from the rack 8 and manually maintained in a disengaged position while simultaneously translating the first arm 2 along the rack in the second direction. In other embodiments, the pawl may include a blocking member that prevents the pawl from re-engaging the rack 8.

Figure 5A:
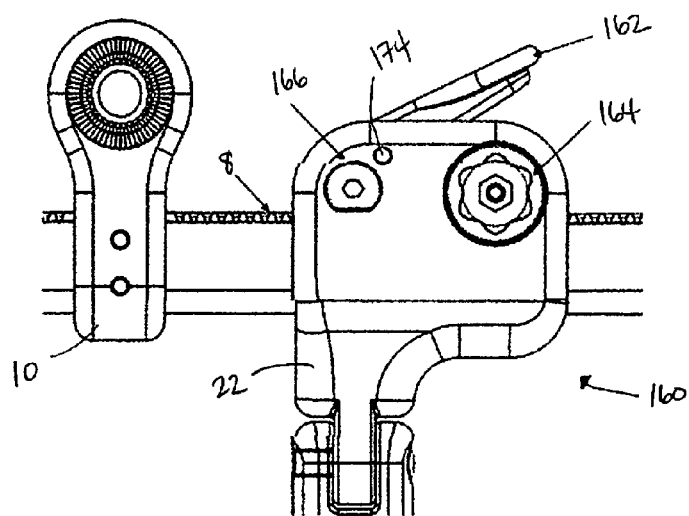
FIG. 5A illustrates a perspective view of a ratcheting assembly as described herein.
Figure 5B:
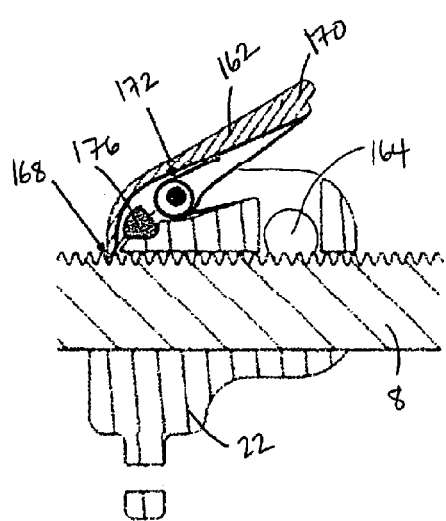
Figure 5C:
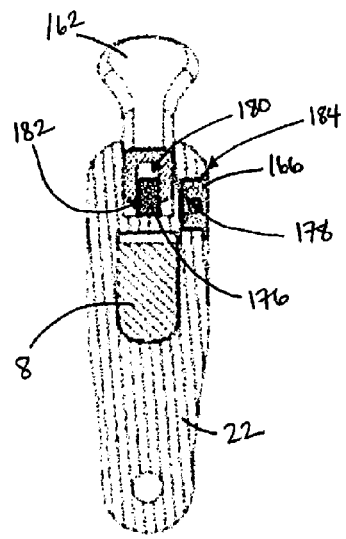

An alternative embodiment of a base is illustrated in FIGS. 5A-F. In these embodiments, the base 22 can include a ratcheting assembly 160. As illustrated in FIGS. 5A-B, the ratcheting assembly 160 can include a pawl 162, a pinion 164, a blocking member 176, and an actuator 166 (e.g., a release button or switch) coupled to the blocking member 176. As illustrated in FIG. 5B, the pawl 162 may include a tip 168 that may be configured to engage the rack 8. Those skilled in the art may appreciate that when the tip 168 is engaged with the rack 8, the first arm 2 may not be able to translate along the rack 8. The pawl 162 may also include a handle 170. The pawl 162 may be configured to pivot about a pin 174, illustrated in FIG. 5A. As illustrated in FIG. 5B, the pawl 162 may be coupled to a torsion spring 172 that causes the tip 168 to pivot towards the rack 8. As illustrated in FIG. 5C, the pawl 162 may include a groove, channel, or cavity 180 therein. The cavity 180 may have an opening 182. The cavity 180 may be configured to receive at least a portion of the blocking member 176 therein, for example, in an interference fit. As illustrated in FIG. 5C, the actuator 166 and/or the blocking member 176 may be coupled to a compression spring 178. The actuator 166 may be at least partially disposed, located, and/or positioned within a depression 184 on the base 22.

The ratcheting assembly 160 may be advantageously configured to be deactivateable, e.g., to transition reversibly between a neutral, deactivated configuration and an activated configuration. In the activated configuration, the first arm 2 may be configured to travel freely (e.g., without interference from and/or simultaneously depressing pawl 162) in one direction along the rack 8. To travel in the opposite direction, the pawl 162 may need to be depressed to a partially-released position, wherein the tip 168 disengages the rack 8, while simultaneously translating the first arm 2 in the opposite direction. If the pawl 162 is not depressed to the partially-released position, and/or if it is released, the first arm 2 may be prevented from translating in the opposite direction. In the neutral, deactivated configuration, the first arm 2 may be configured to travel freely (e.g., without interference from and/or simultaneously depressing pawl 162) in both directions along the rack 8. In both configurations, the first arm 2 may translate by applying torque to the pinion 164, for example, through a driver, such as a screwdriver, wrench, or hex driver.

One example of a ratcheting assembly 160 in the activated configuration is illustrated in FIGS. 5A-C. As illustrated in FIG. 5C, when in the activated configuration, at least a portion of the blocking member 176 may be disposed and/or oriented within the cavity 180 of the pawl 162. When within the cavity 180, the blocking member 176 may not prevent the tip 168 of the pawl 162 from engaging the rack 8.

The ratcheting assembly 160 may be configured to transition from the activated configuration to the neutral, deactivated configuration. For example, in use, a surgeon or other user may deactivate the ratcheting assembly 160 prior to coupling the first arm 2 to the first blade 4 as described herein. Those skilled in the art may appreciate that if the ratcheting assembly 160 were activated, the user might need to keep the pawl 162 in the partially-released position, possibly by hand, while simultaneously driving the actuator 166 and/or coupling the first arm 2 and first blade 4. Advantageously, when in the deactivated configuration, the process may be streamlined, as the user may not need to manually maintain the position of the pawl 162. By enabling the first arm 2 to translate in a more simplified process, the deactivated configuration may thereby promote, enable, and/or encourage easier alignment of the first arm 2 with the first blade 4.

To deactivate the ratcheting assembly 160, the pawl 162 may be depressed to a fully-released position, as illustrated in FIG. 5D-E. As illustrated in FIG. 5E, when the pawl 162 is depressed (e.g., squeezed and/or pressed) to a fully-released position, the blocking member 176 may be released from the cavity 180. Furthermore, the compression spring 178 may be released, which may pull the blocking member 176 away (e.g., out of alignment) from the opening 182 of the cavity 180, and which may also pull the actuator 166 out of the depression 184. As illustrated in FIGS. 5E-F, when in the deactivated configuration, the blocking member 176 may block, inhibit, and/or prevent the pawl 162 from engaging the rack 8.

The ratcheting assembly 160 may also be configured to transition from the deactivated configuration to the activated configuration. For example, in use, a surgeon or other user may activate the ratcheting assembly 160 after coupling the first arm 2 to the first blade 4 as described herein, and/or prior to performing a surgical retraction procedure. Advantageously, activation of the ratcheting assembly 160 may prevent and/or inhibit the first arm 2 from inadvertently translating in a return direction and/or shrinking the retraction window.

To activate (or reactivate) the ratcheting assembly 160, the actuator may be depressed (e.g., pressed and/or pushed) at least partially into the depression 184. The compression spring 178 may be compressed, and the blocking member 176 may be positioned (e.g., pushed) into alignment with the opening 182 of the cavity 180, as illustrated in FIG. 5C.

The rack 8 may be configured to be coupled to a table, cart, tray, and/or other support structure, which can optionally provide increased stability. In these embodiments, table mount 10, as illustrated in FIGS. 1A-B, may be used to couple the rack 8 to the table. In some embodiments, the table mount 10 may include a first engagement member, such as a receptacle, configured to engage or receive the rack 8 therethrough, a second engagement member, such as a receptacle configured to engage or receive a portion of the table therein, and a clamping member configured to couple (e.g., clamp and/or secure) the rack 8 to the table.

In other embodiments, the system 100 may be configured to be handheld. In some embodiments, the first and second arms may be coupled together at a pivot point and/or may be configured to pivot relative to each other. The handheld system may also be self-retaining, e.g., may include a ratchet assembly configured to maintain an angle or relative orientation of the first and second arms.

The first blade 4 may be configured to be reversibly coupled with the first arm 2, as illustrated in FIGS. 1A-B. The retractor system 100 may also include second blade 14, which may be configured to be reversibly coupled with the second arm 12. The first and/or second blades 4, 14 may be generally elongate with a first (e.g., proximal or top) end configured to couple with the first and second arms 2, 12 and a second (e.g., distal or bottom) end configured to engage or contact tissue. As described herein, the first and/or second blades 4, 14 may advantageously be configured to be pivotable relative to the first and/or second arms 2, 12. In some embodiments, the first and/or second blades 4, 14, when coupled to the first and/or second arms 2, 12, may be configured to pivot at an angle in the range of from 1 degree to 360 degrees relative to the first and/or second arms 2, 12. For example, in one embodiment, the first and/or second blades 4, 14, when coupled to the first and/or second arms 2, 12, may be configured to pivot at an angle in the range of from 1 degree to 180 degrees relative to the first and/or second arms 2, 12. In other embodiments, the first and/or second blades 4, 14, when coupled to the first and/or second arms 2, 12, may be configured to pivot at an angle of at least 10, 20, 30, 40, 50, 60, 70, 80, 90, 180 degrees, or more, relative to the first and/or second arms 2, 12.

Figure 3A:
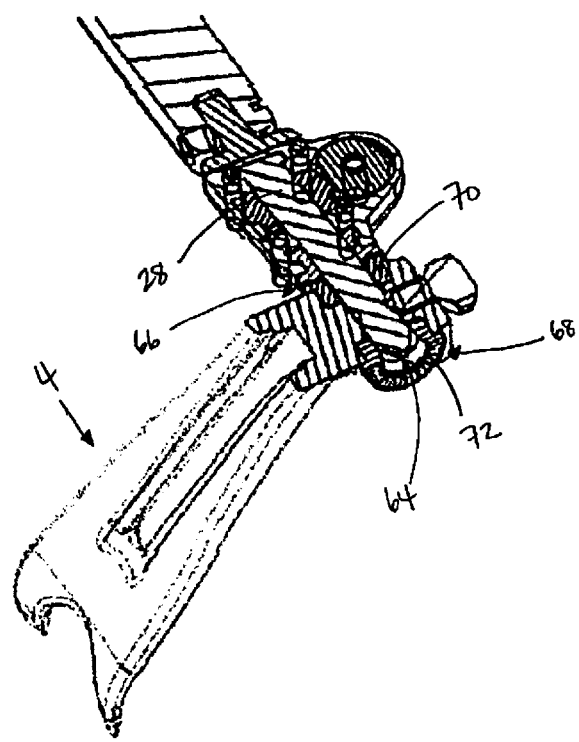
FIG. 3A illustrates a cross-sectional view of a first arm coupled to a first blade as described herein.

Those skilled in the art may appreciate that the second blade 14 may have some or all of the same features as the first blade 4, described herein. As illustrated in FIG. 3A, the first blade 4 can include a through-hole 64 that may be configured to reversibly receive at least a portion of the rotatable shaft 28 therein. The through-hole 64 may be located at the first (e.g., proximal or top) end of the first blade 4. The through-hole 64 can pass transversely across (e.g., parallel to a short axis of) the first blade 4 from a first side surface 66 to a second side surface 68. In some embodiments, the through-hole 64 can include a constant diameter. In other embodiments, it may have a variable diameter. For example, the through-hole 64 can include enlarged first and second openings 74, 76, as illustrated in FIG. 4C.

In some embodiments, the first blade 2 may include a multi-piece construction. For example, the first blade may include a first interface member 70 and a second interface member 72, as illustrated in FIGS. 3A and 4C. The first and second interface members 70, 72 may include at least some of the features of the interface member 26 of the towing assembly 18. For example, the first and second interface members 70, 72 may each include an axial hole. The first and second interface members 70, 72 may be inserted into the first and second openings 74, 76 and the axial holes thereof may at least partially define the through-hole 64. In some embodiments, when in an assembled configuration, the first and second interface members 70, 72 may not be pivotable and/or rotatable relative to the first blade 4.

Figure 4A:
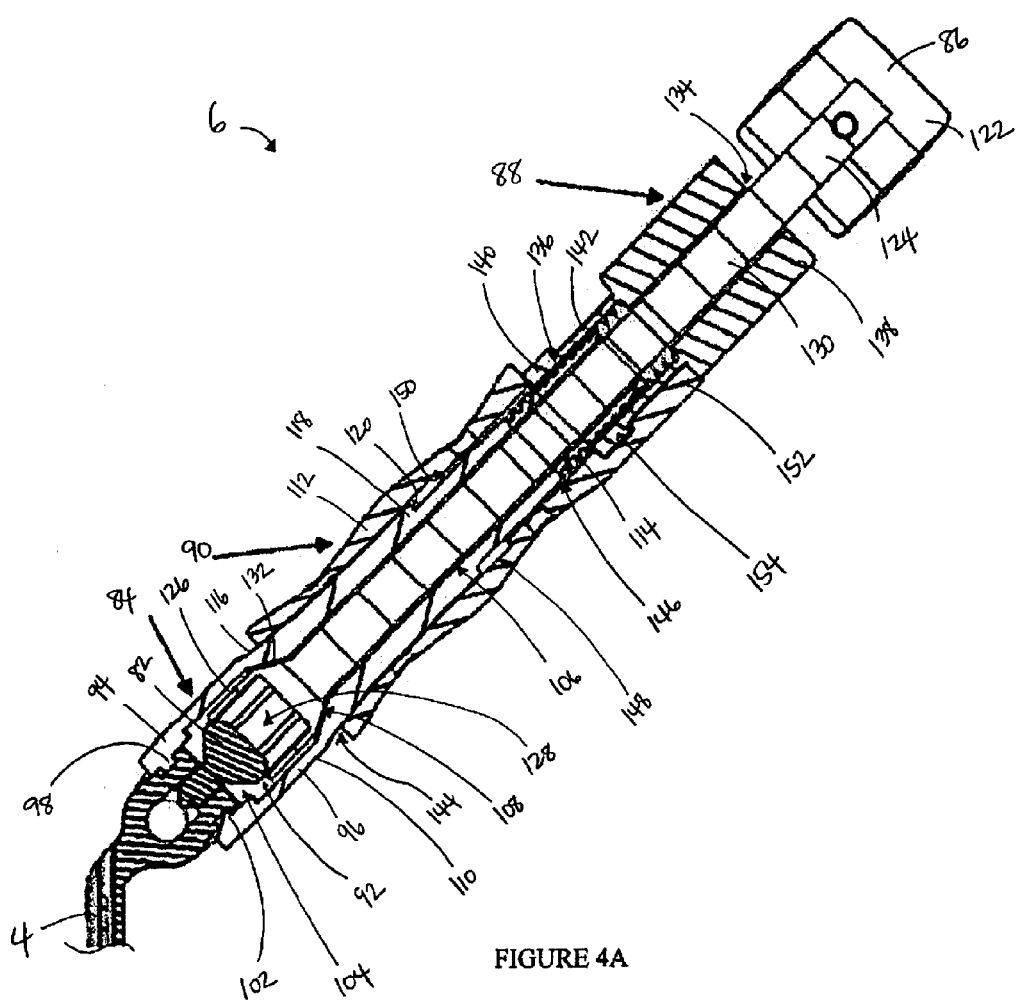
FIG. 4A illustrates a cross-sectional view of a first handle coupled to a first blade as described herein.
Figure 4B:
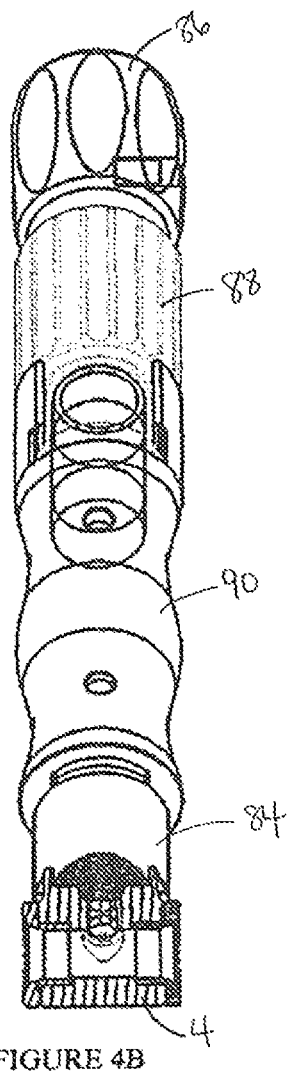
FIG. 4B illustrates a partial cross-sectional view of a first handle coupled to a first blade as described herein.
Figure 4C:
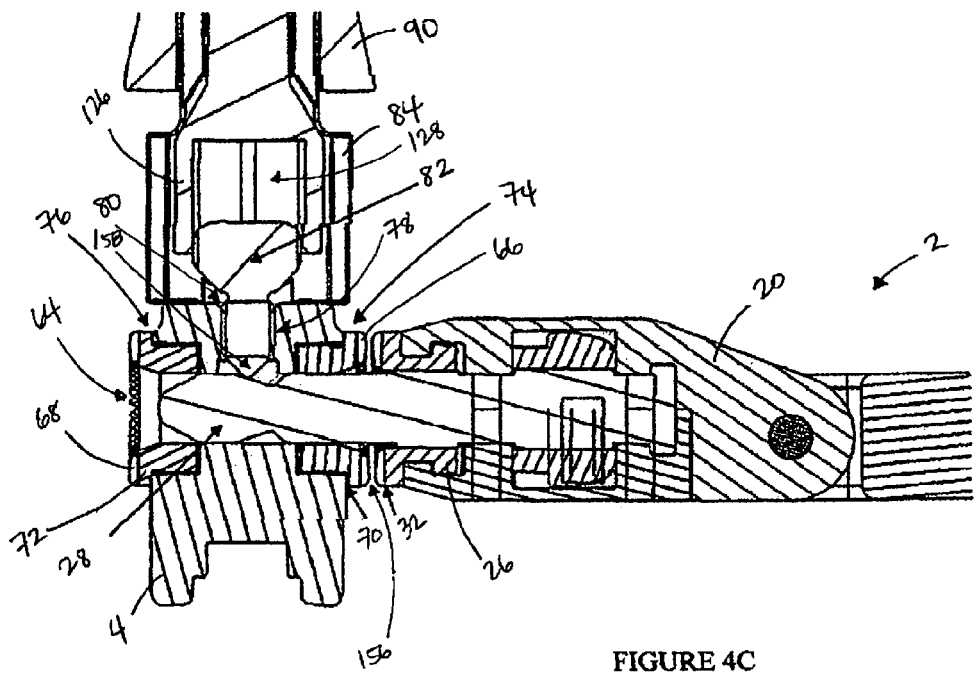
FIGS. 4C-D illustrate cross-sectional views of a first blade, first arm, and first handle as described herein.

The first interface member 70 and the second interface member 72 may each have a first side surface 66 and a second side surface 68, respectively, as illustrated in FIGS. 3A and 4C. The first and/or second side surfaces 66, 68 may include a plurality of protrusions, e.g., bumps, peaks, teeth, and/or ridges, and receptacles, e.g., valleys, channels, depressions, and/or grooves, which may be interspersed therebetween, as illustrated with respect to the second side surface 68 in FIG. 3A. In some embodiments, the protrusions and receptacles may extend radially outward from the through-hole 64. As illustrated in FIG. 3A, the second side surface 68 can include a plurality of ridges and grooves extending radially around an opening of the through-hole 64. As described herein, the plurality of protrusions and receptacles may be referred to as a star grind. The plurality of protrusions and receptacles may advantageously be configured to intermesh and/or interdigitate with the protrusions and receptacles on the distal surface 32 of the first arm 2.

In other embodiments, the first blade 4 may be a unitary body, e.g., the protrusions and receptacles may be machined thereon. Those skilled in the art may appreciate that in these embodiments, the first and second side surfaces 66, 68 may refer to side surfaces of the first blade 4.

In alternative embodiments, the through-hole 64, rather than the first and/or second side surfaces 66, 68, may include a plurality of protrusions and/or receptacles. In these embodiments, the through-hole 64 may include an internal spline (e.g., a plurality of protrusions and/or receptacles) extending longitudinally along an internal surface thereof. Those skilled in the art may appreciate that the internal spline of the through-hole 64 may be configured to mesh and/or interdigitate with the external spline of the rotatable shaft 28, such that rotation of the rotatable shaft 28 may cause rotation of the first blade 4.

As illustrated in FIG. 4C, described further herein, the first blade 4 may include an opening, e.g., passageway 78. Accordingly, in some embodiments, the passageway 78 may be interiorly-threaded. The passageway 78 may have a first opening 80 on a proximal (e.g., top) surface of the blade 4. The passageway 78 may intersect, be perpendicular to, and/or may be in fluid communication with the through-hole 64. The passageway 78 may be configured to receive and/or couple with a retaining member or fastener, such as a set screw 82. As illustrated in FIG. 4C, the set screw 82 may include a stem having a length that is greater than a length of the passageway 78. Accordingly, the stem of the set screw 82 may be configured to enter the through-hole 64. The set screw 82 may be configured to reversibly engage (e.g., couple, mate, and/or contact) the first blade 4 and the rotatable shaft 28 of the first arm 2, for example, by threading into and/or out of the through-hole 64.

In some embodiments, the first blade 4 may include a curved body between the first and second ends that is curved about a longitudinal axis. In other embodiments, the first blade 4 may include a planar body. The second end can include one or more features configured to engage the retracted tissue. In some embodiments, the second end can curve or bend at least partially (e.g., approximately 90 degrees) towards the first end to define a tip that may be configured to cup under or penetrate below the retracted tissue, thereby anchoring or securing the blade and reducing unintentional movement of the system. In some embodiments, the tip may include prongs or teeth. In other embodiments, the tip may be blunt. The tip may be concave, convex, or planar. In some embodiments, the body portion of the first blade 4 may be solid; in other embodiments, it may be fenestrated. The first blade 4 can include rounded, dull, and/or blunt edges that may advantageously minimize and/or reduce trauma to retracted tissue. In some embodiments, the first blade 4 can include at least one longitudinally-extending hole configured to receive one or more instruments such as a Kirschner wire, aspirator, and/or fiber optic light source.

As illustrated in FIG. 1A, in some embodiments the retractor system 100 can include first handle 6. The first handle 6 can be configured to reversibly (e.g., releasably) couple with the first blade 4. Turning to FIGS. 4A-B, the first handle 6 can include a clamping member 84, a rotatable driver 86, an actuator 88, and/or an external sleeve 90.

As illustrated in FIG. 4A, the clamping member 84 can be configured to engage the first blade 4. The clamping member 84 can include a cannula 92 extending axially (e.g., longitudinally) therethrough. The clamping member 84 can include a distal section 110, a proximal section 114, and a middle section 112 therebetween. The middle section 112 can include a tapered section 116 having a tapered outer diameter and/or a cylindrical section 118 having a constant outer diameter. As illustrated in FIG. 4A, the tapered section 116 may be distal to the cylindrical section 118. In these embodiments, the tapered section 116 may be located between the cylindrical section 118 and the distal section 110. The proximal section 114 and/or the distal section 110 may include a constant outer diameter (e.g., may be cylindrical). The distal section 110 may have an outer diameter that is greater than that of the cylindrical section 118. The proximal section 114 may have an outer diameter that is less than that of the cylindrical section 118. Furthermore, the proximal section 114 may be directly adjacent to (e.g., connected to) the cylindrical section 118. In these embodiments, the clamping member 84 may include an exterior shoulder or ledge (e.g., on an outer surface) at the transition point between the proximal section 114 and the cylindrical section 118. As illustrated in FIG. 4A, the proximal section 114 may also include an engagement feature, such as external threading.

The distal section 110 can be split into first and second jaws 94, 96. In embodiments where the distal section 110 has an outer diameter that is greater than that of the cylindrical section 118, the first and second jaws 94, 96 may splay outwards (e.g., away from a longitudinal axis thereof). The first and second jaws 94, 96 may be separated by a longitudinal channel or gap. The first and second jaws 94, 96 and/or the longitudinal channel may be symmetrical. The longitudinal channel may have a width that is variable in some embodiments, and constant in other embodiments. For example, in some embodiments, the longitudinal channel may include an enlarged proximal end, e.g., a proximal section having a width that is greater than that of a distal section thereof. In embodiments where the longitudinal channel includes a constant width, it may also have a rectangular longitudinal cross-section. In some embodiments, the longitudinal channel or gap may be compressible, contractable, and/or constrictable, and may thereby be configured to bring the first and second jaws 94, 96 closer together.

At least one of the first and second jaws 94, 96 can include an inwardly-extending (e.g., radially-extending) projection or protrusion 98, 102 along an inner surface thereof. In some embodiments, the protrusion 98, 102 can define a transverse ledge or shelf along the inner surface of the first and second jaws 94, 96. In some embodiments, the protrusion 98, 102 may be configured to mate with (e.g., be received within) a groove or slot on an outer surface of the first blade 4.

The cannula 92 of the clamping member 84 can include a distal section 104, a proximal section 106, and a tapered section 108 therebetween. In some embodiments, the distal section 104 may have a diameter that is greater than a diameter of the proximal section 106. In other embodiments, the distal section 104 may have a diameter that is less than a diameter of the proximal section 106. The tapered section 108 may be linearly tapered or ramped (e.g., frustoconical). In other embodiments, the tapered section 108 may include a curved tapered surface. The tapered section 108 may be generally overlapping with the tapered section 116 of the clamping member 84.

The rotatable driver 86 can include a knob 122 and a shaft 124 extending therefrom. In some embodiments, the knob 122 may be located at a proximal end and the shaft 124 may extend distally therefrom. The shaft 124 can include a body portion 130 and a distal end 126. The body portion 130 may be an elongate, solid, and/or cylindrical rod. As illustrated in FIG. 4A, at least a portion of the shaft 124 may be configured to extend at least partially through the cannula 92 of the clamping member 84. In some embodiments, the distal end 126 may be enlarged (e.g., may have an outer diameter greater than that of the body portion 130). In these embodiments, the shaft 124 may also include a tapered portion 132 located and configured to transition between the body portion 130 and the distal end 126. The distal end 126 may also include a socket 128. The socket 128 may be configured to receive and/or engage a fastener (e.g., set screw 82) therein. In some embodiments, the socket 128 may include a hexagonal transverse internal cross-section. In use, the rotatable driver 86 may be configured to drive a fastener, e.g., that is disposed within the socket 128. Those skilled in the art may appreciate that the rotatable drive 86 may be configured to rotate and/or spin (e.g., along a longitudinal axis) relative to the clamping member 84.

As illustrated in FIG. 4A, the actuator 88 can include a cannula 134 extending longitudinally (e.g., along a longitudinal axis) therethrough. The cannula 134 can be configured to receive at least a portion of the clamping member 84 and/or rotatable driver 86 therein. The cannula 134 can define an inner surface of the actuator 88. In some embodiments, the interior surface can be configured to engage and/or mate with the clamping member 84. For example, in some embodiments, at least a portion of the interior surface can include threading (e.g., interiorly-threaded portion 136). In these embodiments, the interiorly-threaded portion 136 of the actuator 88 can be configured to engage and/or mate with the threaded proximal section 114 of the clamping member 84.

The actuator 88 can include a proximal section 138, a distal section 140, and a middle section 142 therebetween. In some embodiments, at least one of these sections may include a constant (e.g., cylindrical) outer diameter. In other embodiments, at least one of these sections may include a variable (e.g., tapered) outer diameter. In yet other embodiments, all of these sections may include a constant outer diameter. In these embodiments, the outer diameters of each section may be the same or different (e.g., one or more sections may be larger than others). For example, as illustrated in FIG. 4A, the middle section 142 can have an outer diameter that is less than both an outer diameter of the proximal section 138 and an outer diameter of the distal section 140. The distal section 140 can also have an outer diameter that is less than that of the proximal section 138. In use, the actuator 88 may be configured to rotate relative to the clamping member 84 and/or the external sleeve 90.

The external sleeve 90 may include a cannula 144 extending longitudinally (e.g., along a longitudinal axis) therethrough. The cannula 144 may be configured to receive at least a portion of the clamping member 84 therein. The cannula 144 can define an inner surface of the external sleeve 90. The cannula 144 may have a constant or variable diameter. In some embodiments, the cannula 144 may include two or more sections, each having a different, constant diameter. For example, the cannula 144 may include a plurality of cylindrical sections, each having a different diameter. As illustrated in FIG. 4A, the cannula 144 can include a proximal section 146 and a distal section 148. The proximal and distal sections 146, 148 may each include a constant diameter. Additionally, the diameter of the proximal section 146 of the cannula 144 may be less than that of the distal section 148. Accordingly, the external sleeve 90 may include an internal shoulder or ledge 150 at a transition point between the proximal and distal sections 146, 148.

The external sleeve 90 may also include a proximal extension member 152, as illustrated in FIG. 4A. The proximal extension member 152 may extend from at least a portion of a proximal end thereof. In some embodiments, the proximal extension member 152 may take the shape of a longitudinal section of a hollow cylinder, hose, or pipe. The proximal extension member 152 may have a curved inner surface that curves along a longitudinal axis thereof. The curved inner surface may have a radius of curvature that is equal to or slightly larger than a radius of curvature of the middle section 142 of the actuator 88. The proximal extension member 152 may further include a partially-circumferential (e.g., C-shaped) inner groove 154. In some embodiments, at least a portion of the actuator 88 may be configured to engage with, interlock with, and/or nest in at least a portion of the proximal extension member 152. For example, the distal section 140 of the actuator 88 may be configured to be received within the inner groove 154 of the external sleeve 90. As a result, the actuator 88 and the external sleeve 90 may be configured to translate (e.g., slide) together longitudinally. Additionally, the actuator 88 and/or external sleeve 90 may be configured to rotate or spin relative to each other, wherein the distal section 140 of the actuator 88 may rotate or spin within the inner groove 154 of the external sleeve 90.

Embodiments herein are also directed to methods of installing and/or using the retractor system 100. The retractor systems described herein may be used in a wide variety of surgical procedures to retract tissue and/or maintain or enlarge a surgical window. In some embodiments, the retractor systems may be used in a spinal surgery, such as a fusion or disc replacement procedure. The retractor systems may be used in fusion procedures that approach a patient's spine from a variety of different angles (e.g., anterior, posterior, lateral, and/or transforaminal). In some embodiments, the retractor systems may be used or installed as part of a midline-incision transforaminal (e.g., TLIF) approach. In these embodiments, a user may make a midline incision along a spinous process. Using a cannula or muscle dissector, the user may release the multifidis muscle from the spinous process and measure for the appropriate blade length before installing and/or using the retractor system 100 (e.g., before reversibly coupling the first blade 4 to the first handle 6 and/or first arm 2).

Figure 4D:
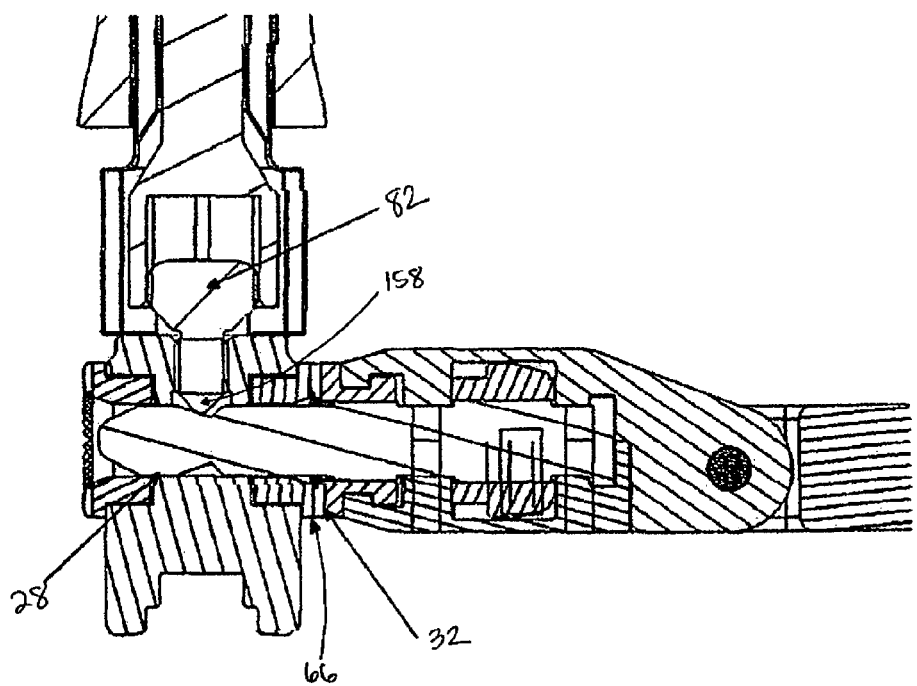

Embodiments directed to methods of installing and/or using the retractor system 100 may include the step of providing a retractor system as described herein that includes first arm 2, first blade 4, and/or first handle 6. These embodiments can also include reversibly coupling the first blade 4 with the first handle 6. This step can include inserting at least a portion of the first blade 4 between the first and second jaws 94, 96 of the clamping member of the first handle 6, as illustrated, for example, in FIGS. 4A-B. In some embodiments, the first and second jaws 94, 96 may include an internal protrusion 98, 102, as described herein. In these embodiments, this step can also include inserting or mating the protrusion 98, 102 with a corresponding groove or channel on the first blade 4. In some embodiments, the first blade 4 may also include a set screw 82 that is at least partially threaded into passageway 78, as illustrated in FIGS. 4C-D, described further herein. In these embodiments, the step of reversibly coupling the first handle 6 to the first blade 4 may include coupling the set screw 82 with the rotatable driver 86, for example, by inserting a head of the set screw 82 at least partially into socket 128 on the distal end 126 of the shaft 124 of the rotatable driver 86, as illustrated in FIG. 4A. Those skilled in the art may appreciate that in this configuration, rotation of the rotatable driver 86 may result in rotation of the set screw 82, thereby causing the set screw 82 to travel through the passageway 78.

Once the first blade 4 is positioned between the first and second jaws 94, 96, the first and second jaws 94, 96 may be tightened, secured, and/or engaged around the portion of the first blade 4 that is disposed therebetween. This step may include rotating the actuator 88 of the first handle 6 in a first direction. As illustrated in FIG. 4A, as the actuator 88 is threaded along the clamping member 84 in a first direction (e.g., downwards and/or distally), the actuator 88 may push the external sleeve 90 in the same direction. The external sleeve 90 may translate and/or slide over the clamping member 84. As described herein, in some embodiments, the clamping member 84 may include a cylindrical section 118, a distal section 110, and a tapered section 116 therebetween. The distal section 110 can have a larger outer diameter than the cylindrical section 118. Tapered section 116 can have a variable outer diameter that is equal to that of the cylindrical section 118 at a proximal end and equal to that of the distal section 110 at a distal end (e.g., the tapered section 116 may have an outer diameter that increases in a distal direction). As the external sleeve 90 passes over the tapered section 116, it may compress the longitudinal channel separating the first and second jaws 94, 96, thereby squeezing and/or clamping the first and second jaws 94, 96 together around the first blade 4. The external sleeve 90 may continue to travel distally until the inner ledge 150 of the external sleeve 90 contacts the outer ledge 120 of the clamping member 84.

Advantageously, the coupled first handle 6 and first blade 4 may be used as an independent device for handheld retraction, and may be referred to herein as a handheld retractor assembly. Thus, in some embodiments, the method of installing and/or using the retractor system 100 may include manually positioning the reversibly-coupled first handle 6 and first blade 4, which may include manually retracting tissue, prior to reversibly coupling the first blade 4 to the first arm 2. In some embodiments, the second handle 16 and second blade 14 may also be reversibly coupled and manually positioned along with the coupled first handle 6 and first blade 4. In some embodiments, the handheld retractor assembly may advantageously provide a user or operator with increased freedom and/or improved blade manipulation, as compared to, for example, a retractor system that is solely configured for linear retraction via mounting to an arm, frame, or other scaffolding.

The first blade 4 may then be reversibly coupled to the first arm 2. When the first blade 4 is coupled to the first arm 2, the first blade 4 may be configured to rotate with the rotating shaft 28 and/or interface member 26. Additionally, the first blade 4 may not be able to rotate independently from the rotatable shaft 28 and/or the interface member 26. This step may include inserting the rotatable shaft 28 of the first arm 2 into the through-hole 64 of the first blade 4, as illustrated in FIGS. 4C-D. The retaining member (e.g., set screw 82) may then be threaded at least partially through the passageway 78 on the first blade 4. Any suitable driver may be used to thread the set screw 82 through the passageway 78 of the first blade 4. In some embodiments, this step may be accomplished at least in part by rotating the rotatable driver 86, which may apply torque to the set screw 82.

The step of threading the set screw 82 at least partially through the passageway 78 may include threading the set screw 82 to a first position wherein the first blade 4 is fastened to the first arm 2, as illustrated in FIG. 4C. In this position, the first blade 4 and the first arm 2 may be connected, but the first side surface 66 of the first blade 4 may be spaced apart from the outer surface 32 of the interface member 26 of the first arm by a gap 156. This position may advantageously enable a surgeon or other user to make additional manipulations and/or adjustments to the orientation and/or location of the first blade 4 prior to coupling it to the first arm 2. As the set screw 82 continues to be threaded through the passageway 78, a tip 158 of the set screw 82 may engage the rotatable shaft 28 and pull the rotatable shaft 28 towards the first blade 4. The set screw 82 may continue to be threaded through the passageway 78 until it achieves a second position, illustrated in FIG. 4D, wherein the tip 158 of the set screw 82 is nested within the circumferential groove 36 of the rotatable shaft 28. As the rotatable shaft 28 is pulled toward the first blade 4, the interface member 26 may also be pulled towards the first blade 4. Thus, at this position, the protrusions and receptacles (e.g., star grind) of the first side surface 66 of the first blade 4 may intermesh and/or interdigitate with the protrusions and receptacles (e.g., star grind) of the distal surface 32 of the first arm 2. Those skilled in the art may appreciate that the star grinds may advantageously self-align, e.g., they can intermesh in the absence of pre-alignment by a surgeon or other user.

As described herein, the first blade 4 and the first handle 6 may be reversibly coupled. After the first blade 4 is reversibly coupled to the first arm 2, the first handle 6 may be uncoupled (e.g., disengaged) from the first blade 4. To uncouple the first blade 4 and the first handle 6, the actuator 88 of the first handle 6 may be rotated in a second direction, which may cause the actuator 88 to be threaded along the clamping member 84 in a second direction opposite the first (e.g., upwards and/or proximally). The actuator 88 may pull the external sleeve 90 in the same direction, thereby releasing the external sleeve 90 from the tapered section 116 of the clamping member 84. Additionally, as the actuator 88 continues to travel in an upwards and/or proximal direction, it may exert an upwards and/or proximally-directed force on the knob 122 of the rotatable driver 86. The rotatable driver 86 may then be pulled proximally. The tapered section 132 of the rotatable driver 86 may then contact and/or exert force on an inner surface of the external sleeve 90 at the tapered section 108 of the cannula 92. This force may expand the longitudinal channel separating the first and second jaws 94, 96, thereby splaying the first and second jaws 94, 96 apart.

The first blade 4 may then be towed (e.g., pivoted) relative to the first arm 2 or a portion thereof (e.g., body 20), for example, by actuating the towing assembly 18 or a component thereof. The first blade 4 may be towed about the rotatable shaft 28 (e.g., towed about a pivot point defined by a longitudinal axis thereof). As the first blade 4 is towed, the first arm 2 may advantageously not move with respect to the retraction site. The step of actuating the towing assembly 18 can include actuating the worm drive. The step of actuating the worm drive can include applying torque to an actuator 42, such as a hex head, coupled to worm 38. As the actuator 42 is rotated, the rotational force may be transmitted to the worm 38. The rotating worm 38 may engage the worm gear 40 and cause the worm gear 40 to rotate about an axis perpendicular and/or orthogonal to that of the worm 38. Rotation of the worm gear 40 may cause the rotatable shaft 28 and interface member 26 to rotate. As the interface member 26 may be intermeshed with the first blade 4, rotation of the interface member 26 may cause the first blade 4 to rotate.

Advantageously, this mechanism may enable the first blade 4 to be towed relative to the first arm 2 at any angle (e.g., between 0 and 360 degrees). In some embodiments, the first blade 4 may be towed relative to the first arm 2 from a first position to a second position, wherein the second position is in the range of from 1 degree to 360 degrees away from the first position. In other embodiments, the first blade 4 may be towed relative to the first arm 2 from a first position to a second position, wherein the second position is in the range of from 1 degree to 180 degrees away from the first position. In still other embodiments, the first blade 4 may be towed relative to the first arm 2 from a first position to a second position, wherein the second position is in the range of from 1 degree to 90 degrees away from the first position. In yet other embodiments, the first blade 4 may be towed relative to the first arm 2 from a first position to a second position, wherein the second position is at least 90 degrees away from the first position.

Some embodiments may further include adjusting a vertical position of the first blade 4 (e.g., relative to a surgical site). As described herein, the first arm 2 may include a plurality of pivot points. Thus, these embodiments may include bending and/or flexing the first arm 2, for example by pivoting the body 20 relative to the connector 24 and/or pivoting the connector 24 relative to the base 22.

Some embodiments may further include coupling the first arm 2 to the rack 8. This step may include inserting the rack 8 into the base 22 of the first arm 2. The first arm 2 may then be translated, e.g., linearly, along the rack. In some embodiments, the first arm 2 may be translated in one direction (e.g., lateral). In other embodiments, it may be also translated in a second, opposite direction (e.g., medial). The first arm 2 may be translated along the rack 8 by engaging (e.g., turning and/or rotating) actuator 62, as illustrated, for example, in FIG. 1B. Actuator 63 may be used to translate second arm 12 along the rack 8. In some embodiments, as the actuator 62 is turned in a first direction, the translation member (e.g., pinion) may also rotate, engaging the teeth on the rack 8, and the first arm 2 may then be translated in a first direction. In some embodiments, the first arm 2 may be translated in a second, opposite direction by turning and/or rotating the actuator 62 in an opposite direction. Some embodiments can also include locking the position of the first arm 2 along the rack 8. In some embodiments, this step may include engaging a locking member so as to clamp the translation member and/or rack 8.

In embodiments that include ratcheting assembly 160, the step of translating the first arm 2 along the rack 8 in a first and/or second direction can include activating or deactivating the ratcheting assembly 160 as described herein. Some embodiments may include deactivating the ratcheting assembly 160, for example, prior to coupling the first arm 2 and first blade 4. The deactivating step may include depressing the pawl 162 to a fully-released position as described herein. The first arm 2 may then be subsequently translated. When the ratcheting assembly 160 is in the deactivated configuration, the first arm 2 may be configured to translate freely (e.g., without interference from and/or simultaneously depressing pawl 162) in both directions.

Some embodiments may include activating the ratcheting assembly 160, for example, after coupling the first arm 2 and first blade 4. The activating step may include depressing actuator 166 as described herein. When the ratcheting assembly 160 is in the activated configuration, the first arm 2 may be configured to translate freely in one direction, and may be configured to translate in the other direction only when simultaneously depressing the pawl 162 to a partially-released position as described herein. In any of these embodiments, the first arm 2 may be translated by engaging (e.g., rotating) pinion 164, for example, with a hex driver or other type of driver.

Some embodiments may further include reversibly coupling the rack 8 to a support structure, such as a table. This step may include coupling (e.g., clamping) the rack 8 to table mount 10, and coupling (e.g., clamping) the table mount 10 to the support structure.

Those skilled in the art may appreciate that in some embodiments, one or more of the steps described herein may take place in a different sequence. For example, the first arm 2 may be coupled to the rack 8 prior to coupling one or both blades to an arm and/or a handle (e.g., prior to coupling the first blade 4 to the first arm 2 and/or first handle 6). Additionally, the rack 8 may be coupled to the support structure prior to coupling the rack 8 to one or both arms, and/or prior to coupling one or both blades to an arm and/or a handle.

Advantageously, the retractor system and associated devices described above can be used with a number of different implants and devices. For example, the retractor system can be used to provide access to a surgical site such that a prosthetic device that preserves motion can be provided. In addition, the retractor system can be used to provide access to a surgical site such that a fusion device, such as a cage or spacer, can be provided. In addition, the retractor system can be used to provide access to various other devices, including but not limited to rods, screws (e.g., pedicle screws), plates and various other implants that are used in spine surgery.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims. Although individual embodiments are discussed herein, the invention covers all combinations of all those embodiments.

What is claimed is:

1. A retractor system comprising:
   a first arm comprising a towing assembly, the towing assembly comprising an interface member coupled to a rotatable shaft, wherein the interface member comprises a distal surface having a plurality of protrusions and receptacles; and
   a first blade comprising a through-hole passing from a first side surface to a second side surface and configured to reversibly receive the rotatable shaft therein, wherein the first blade comprises a plurality of protrusions and receptacles configured to intermesh with the plurality of protrusions and receptacles of the distal surface of the first arm.

2. The retractor system of claim 1, wherein the first arm comprises a body, a base, and a connector pivotably coupled therebetween, and wherein the towing assembly is located at least partially within the body.

3. The system of claim 2, wherein the system further comprises a rack, and wherein the base is configured to couple the arm to the rack.

4. The system of claim 3, further comprising a table mount configured to couple to the rack.

5. The system of claim 2, wherein the base comprises a deactivateable ratcheting assembly, the deactivateable ratcheting assembly comprising a pinion configured to engage the rack, a pawl, a blocking member, and an actuator coupled to the blocking member.

6. The retractor system of claim 1, wherein the rotatable shaft comprises a circumferential groove on an exterior surface thereof.

7. The retractor system of claim 1, wherein the distal surface of the interface member comprises a star grind.

8. The system of claim 1, wherein the distal surface of the interface member comprises a plurality of radially-extending ridges and grooves.

9. The system of claim 1, wherein the towing assembly further comprises a worm drive comprising a worm and a worm gear, and wherein the worm gear is configured to couple to the rotatable shaft.

10. A retractor system, comprising:
    a first arm comprising a towing assembly, the towing assembly comprising a rotatable shaft coupled to both a worm drive and an interface member, the interface member comprising a star grind;
    a first blade comprising a through-hole passing from a first side surface to a second side surface and configured to reversibly receive the rotatable shaft therein, an interiorly-threaded passageway that intersects the through-hole, and a star grind on the first side surface configured to interdigitate with the star grind of the first arm; and
    a retaining member configured to reversibly engage the interiorly-threaded opening of the first blade and the rotatable shaft of the first arm.

11. The system of claim 10, wherein the second side surface comprises a plurality of protrusions and receptacles.

12. The system of claim 10, wherein the interiorly-threaded passageway comprises an opening on a proximal surface of the blade.

13. The system of claim 10, wherein the first blade comprises a concave distal end.

14. A retractor system, comprising:
    a first arm comprising a towing assembly, the towing assembly comprising a rotatable shaft coupled to both a worm drive and an interface member, the interface member comprising a star grind; and
    a first blade comprising a through-hole configured to reversibly receive the rotatable shaft therein and a star grind configured to interdigitate with the star grind of the first arm;
    wherein the first blade is configured to be pivotable relative to the first arm by an angle of at least 180 degrees when the first blade is coupled to the first arm.

15. The system of claim 14, further comprising a first handle configured to reversibly couple with the first blade, wherein the first handle comprises:
    a clamping member configured to engage the first blade and comprising a cannula extending therethrough;
    a rotatable driver comprising a knob and a shaft extending therefrom, the shaft configured to extend at least partially through the cannula of the clamping member;
    an actuator comprising a cannula configured to receive at least a portion of the clamping member therein; and
    an external sleeve comprising a cannula extending therethrough, the cannula configured to receive at least a portion of the clamping member therein.

16. The system of claim 15, wherein a distal end of the clamping member comprises first and second jaws separated by a longitudinal channel.

17. The system of claim 15, wherein a distal end of the shaft of the rotatable driver comprises a socket.

18. The system of claim 15, wherein the rotatable driver is configured to rotate relative to the clamping member.

19. The system of claim 15, wherein the actuator is configured to rotate relative to the clamping member and the external sleeve.

20. The system of claim 15, wherein the external sleeve comprises a proximal extension member that extends from at least a portion of a proximal end thereof, and wherein the proximal extension member comprises a circumferential inner groove.

* * * * *